(12) United States Patent
Boyle et al.

(10) Patent No.: US 6,890,936 B2
(45) Date of Patent: May 10, 2005

(54) MUSCARINIC ANTAGONISTS

(75) Inventors: Craig D. Boyle, Branchburg, NJ (US); William J. Greenlee, Teaneck, NJ (US); Samuel Chackalamannil, Califon, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/425,376

(22) Filed: Apr. 28, 2003

(65) Prior Publication Data

US 2004/0067972 A1 Apr. 8, 2004

Related U.S. Application Data

(60) Provisional application No. 60/376,093, filed on Apr. 26, 2002.

(51) Int. Cl.[7] .................... C07D 211/06; A61K 31/555
(52) U.S. Cl. ........................ 514/316; 645/186
(58) Field of Search ........................ 546/186; 514/316

(56) References Cited

FOREIGN PATENT DOCUMENTS

EP  0456183  11/1991

OTHER PUBLICATIONS

J. Baumgold et al., 3–α–Chlorimperialine: an m2–selective muscarinic receptor antagonist that penetrates into brain, *European Journal of Pharmacology*, (1994), 251:315–317.

C. Melchiorre et al., Synthesis and Biological Activity of Some Methoctramine–Related Tetraamines Bearing a 11–Acetyl–5, 11–dihydro–6H–pyrido . . . ,*J. Med. Chem.*, (1993), 36:3734–3737.

M. Watson et al., [3H] pirenzepine and (–)–[3H] quinuclidinyl benzilato binding to rat cerebral cortical and cardiac muscarinic cholinergic sites, *J. Pharmacol. Exp. Ther.*, (1986), 237:419–427.

PCT International Search Report dated Apr. 24, 2003 for corresponding PCT Application No. PCT/US/03/12694.

*Primary Examiner*—Rita Desai
(74) *Attorney, Agent, or Firm*—Robert L. Bernstein; William Y. Lee

(57) ABSTRACT

The invention described herein are compounds in accordance with formula I:

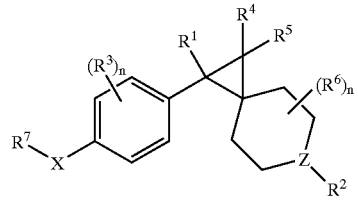

wherein $R^1$, $R^2$, $R^3$, $R^4$, $R^5$, $R^6$, $R^2$, $R^8$, $R^9$, n, X, and Z are as defined herein, pharmaceutical compositions containing at least one compound of formula I, methods of preparation thereof, and methods of treating disorders with at least one compound of formula I or at least one compound of formula I in association with at least one acetylcholinesterase inhibitor.

26 Claims, No Drawings

MUSCARINIC ANTAGONISTS

CROSS REFERENCE TO RELATED APPLICATION

This application claims priority to U.S. Provisional Application No. 60/376,093, filed Apr. 26, 2002.

FIELD OF THE INVENTION

The present invention relates to 1,4-di-substituted piperidines useful in the treatment of cognitive disorders, pharmaceutical compositions containing the compounds, methods of treatment using the compounds, and to the use of said compounds in combination with acetylcholinesterase inhibitors.

BACKGROUND OF INVENTION

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize $M_2$ muscarinic receptors, especially in relation to $M_1$ muscarinic receptors, should possess activity against cognitive disorders. Baumgold et al. (Eur. J. of Pharmacol., 251, (1994) 315–317) disclose 3-α-chloroimperialine as a highly selective $M_2$ muscarinic antagonist.

The present invention is predicated on the discovery of a class of 1,4-di-substituted piperidines, having $M_2$ selectivity.

SUMMARY OF THE INVENTION

The present invention provides a novel class of compounds as antagonists of the muscarinic receptor, methods of preparing such compounds, pharmaceutical compositions containing one or more such compounds, methods of preparing pharmaceutical formulations comprising one or more such compounds, and methods of treatment, prevention or amelioration of one or more diseases associated with the muscarinic receptor. In one embodiment, the present application relates to a compound having the general structure shown in Formula I:

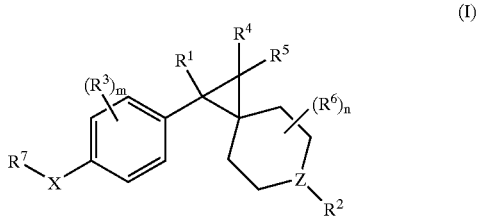

(I)

or pharmaceutically acceptable salts or solvates thereof; wherein:

$R^1$ is selected from the group consisting of H, alkyl, alkenyl and alkynyl;

$R^2$ is

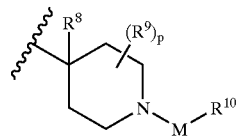

p is 0–4;
m is 0–4;
n is 0–4;

$R^3$ is selected from the group consisting of H, alkyl, halo, alkoxy, hydroxy, nitro, aminoalkyl, and acyl, wherein $R^3$ can be the same or different and is independently selected when m is 2–4;

$R^4$ and $R^5$, which can be the same or different, are each independently selected from the group consisting of H and halogen;

$R^6$ is selected from the group consisting of H, halo, alkyl, hydroxy, hydroxyalkyl, arylalkyl, aminoalkyl, haloalkyl, and thioalkyl, wherein $R^6$ can be the same or different and is independently selected when n is 2–4;

$R^7$ is selected from the group consisting of hydrogen, acyl, alkyl, alkoxy, alkenyl, cycloalkyl, cycloalkyl substituted with 0–2 alkyl groups which can be the same or different and are independently selected, cycloalkenyl, bicycloalkyl, arylalkenyl and arylalkyl;

$R^8$ is selected from the group consisting of H, alkyl, aryl, heteroaryl, halo, and cycloalkyl;

$R^9$ is selected from the group consisting of H, alkyl, aryl, halo, hydroxy and cycloalkyl, wherein $R^9$ can be the same or different and is independently selected when (p) is 2–4, or two $R^9$ groups can be joined together to form the group —$(CH_2)_r$—, wherein r is 1 to 6;

$R^{10}$ is selected from the group consisting of substituted or unsubstituted alkyl, substituted or unsubstituted aryl, and substituted or unsubstituted heteroaryl, with the proviso that when $R^{10}$ is a substituted or unsubstituted heteroaryl, the bond to M is from a carbon atom in the $R^{10}$ group;

Z is N or C—$R^1$;

X is selected from the group consisting of —O—, —S—, —S(O)—, —S(O)$_2$—, —C(O)—, -alkylene-, —C(S)—, —C(alkyl)$_2$- and —C(H)(alkyl)-; and M is —S(O)$_2$— or —C(O)—.

When $R^{10}$ is a substituted aryl or substituted heteroaryl, the term substituted preferably means being substituted with one or more groups which can be the same or different and are independently selected from the group consisting of halogen, lower alkyl and amino group.

Another aspect of the invention relates to a pharmaceutical composition which comprises at least one compound of formula I, preferably in association with at least one pharmaceutically acceptable carrier.

Another aspect of the invention relates to a method of making a pharmaceutical composition comprising contacting at least one compound of formula I with at least one pharmaceutically acceptable carrier.

Another aspect of the invention relates to a method of treating a cognitive or neurodegenerative disease comprising administering to a patient suffering from said disease at least one compound of formula I.

Another aspect of the invention relates to a method of treating a cognitive or neurodegenerative disease comprising administering to a patient suffering from said disease a combination of at least one compound of formula I in association with at least one acetylcholinesterase inhibitor.

Another aspect of the invention relates to a kit for treating a cognitive or neurodegenerative disease comprising in a single package a first container and a second container for use in combination, said first container comprising at least one compound of formula I and said second container comprising at least one acetylcholinesterase inhibitor.

DETAILED DESCRIPTION

The present invention provides a novel class of compounds as antagonists of the muscarinic receptor ($M_2$ and/or $M_4$), methods of preparing such compounds, pharmaceutical compositions containing one or more such compounds, methods of preparing pharmaceutical formulations comprising one or more such compounds, and methods of treatment, prevention or amelioration of one or more diseases associated with the muscarinic receptor.

In one embodiment, the present application relates to a compound having the general structure shown in Formula I:

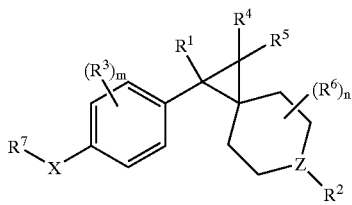

(I)

or pharmaceutically acceptable salts or solvates thereof, wherein X, Z, $R^1$, $R^2$, $R^3$, $R^4$, $R^5$, $R^6$, $R^7$, m and n are as defined above.

In one embodiment, Z is N.

In another embodiment, $R^7$ is alkyl. In yet another embodiment, $R^7$ is —CH(CH$_3$)$_2$.

In another embodiment, $R^3$ is H, alkyl or halo. In yet another embodiment, $R^3$ is H.

In another embodiment, $R^6$ is H or alkyl. In yet another embodiment, $R^6$ is H.

In another embodiment, $R^1$ is H or alkyl. In yet another embodiment, $R^1$ is H or Me.

In another embodiment, X is selected from the group consisting of —O—, —S—, —S(O)— and —S(O)$_2$—. In yet another embodiment, X is —O—.

In another embodiment, $R^8$ is H or alkyl. In yet another embodiment, $R^8$ is H.

In another embodiment, $R^9$ is H or alkyl. In yet another embodiment, $R^9$ is H.

In yet another embodiment, $R^{10}$ is preferably a substituted or unsubstituted alkyl, or substituted or unsubstituted aryl, more preferably a substituted aryl. In this embodiment, substituted aryl preferably means substituted with one or more groups which can be the same or different, each being independently selected from the group consisting of alkyl, halogen and amino.

Examples of specific compounds of this invention are represented by the formula:

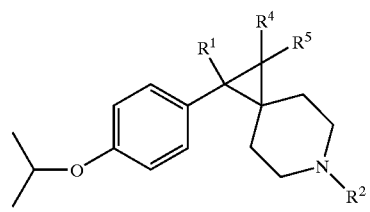

wherein $R^1$, $R^2$, $R^4$ and $R^5$ are defined in Table 1 below:

TABLE 1

| # from table of compounds | $R^1$ | $R^2$ | $R^4$ | $R^5$ |
|---|---|---|---|---|
| 1 | H | (2-Cl, 3-Me benzoyl piperidine) | Cl | Cl |
| 2 | H | (3-Cl, 2-Me benzoyl piperidine) | Cl | Cl |
| 3 | H | (2,3-diCl benzoyl piperidine) | Cl | Cl |
| 4 | H | (2-NH$_2$, 3-Me benzoyl piperidine) | Cl | Cl |
| 5 | H | (2-NH$_2$, 3-Cl benzoyl piperidine) | Cl | Cl |
| 6 | H | (2-NH$_2$, 3-F benzoyl piperidine) | Cl | Cl |

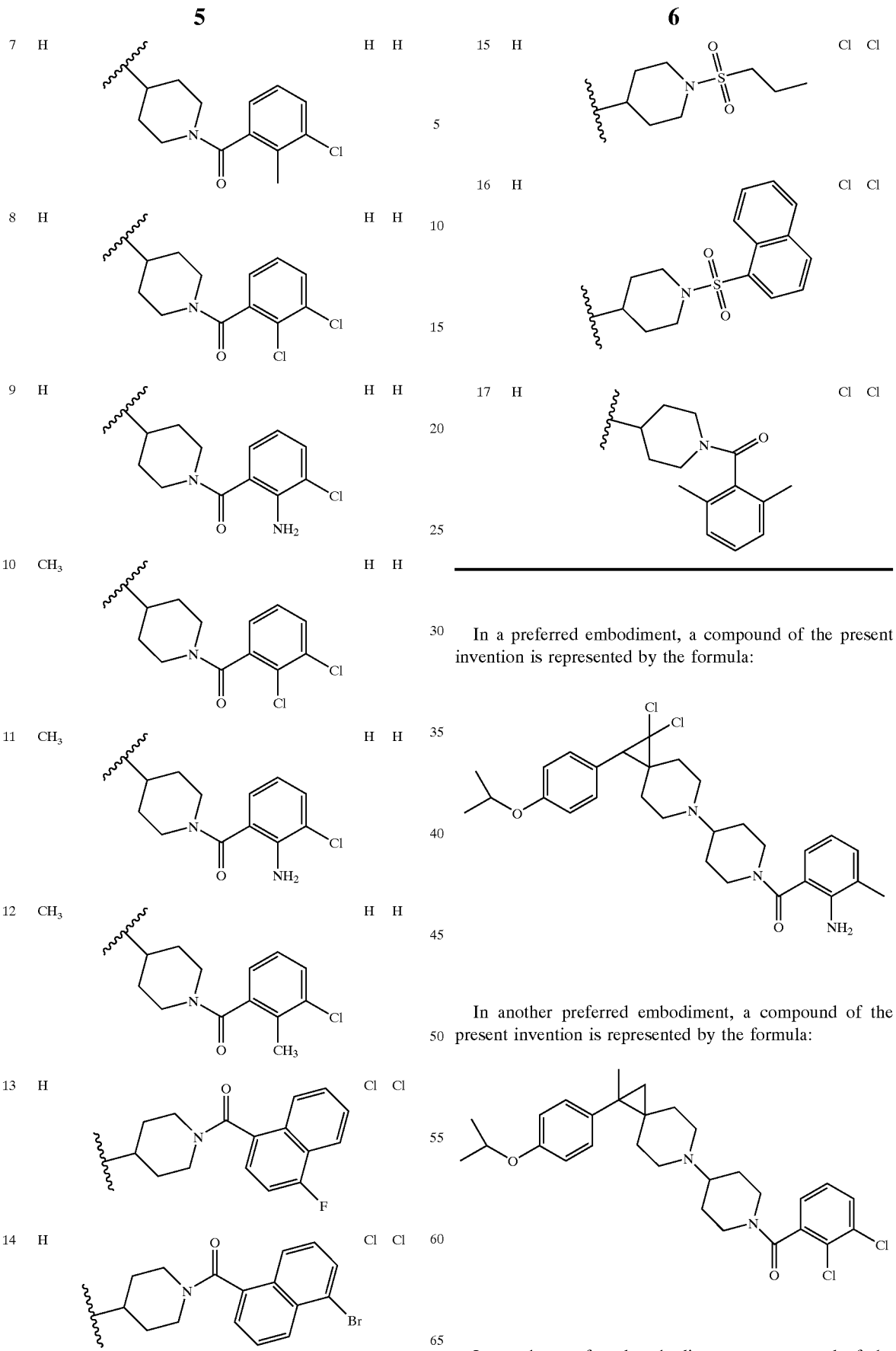
In a preferred embodiment, a compound of the present invention is represented by the formula:
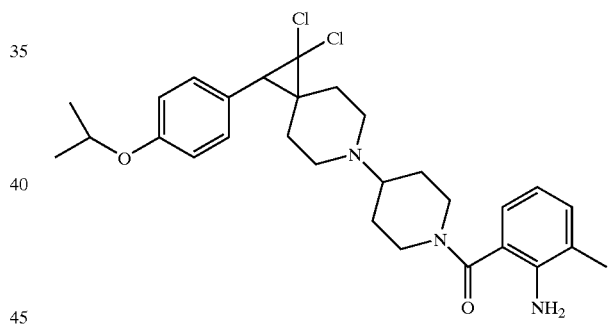
In another preferred embodiment, a compound of the present invention is represented by the formula:
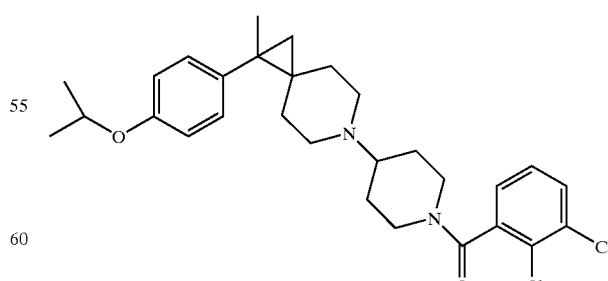
In another preferred embodiment, a compound of the present invention is represented by the formula:

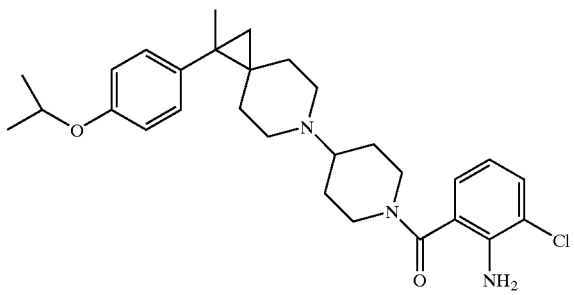

In yet another preferred embodiment, a compound of the present invention is represented by the formula:

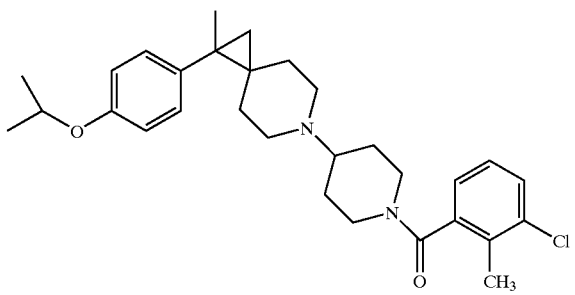

Except where stated otherwise, the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

"Alkyl" means an aliphatic hydrocarbon group which may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched alkyl means that one or more lower alkyl groups such as methyl, ethyl or propyl, are attached to a linear alkyl chain. "Lower alkyl" means a group having 1 to 6 carbon atoms in the chain which may be straight or branched. The alkyl may be substituted which means that the alkyl group can be substituted by one or more substituents which may be the same or different, each substituent being independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising 2 to about 15 carbon atoms in the chain. Preferred alkenyl groups have 2 to about 12 carbon atoms in the chain; and more preferably 2 to about 6 carbon atoms in the chain. Branched means that one or more lower alkyl groups such as methyl, ethyl or propyl, are attached to a linear alkenyl chain. "Lower alkenyl" means 2 to about 6 carbon atoms in the chain which may be straight or branched. The alkenyl may be substituted and the term "substituted alkenyl" means that the alkenyl group may be substituted by one or more substituents which can be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, and n-pentenyl.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, phenethyl and naphthalenylmethyl. The aralkyl is linked to an adjacent moiety through the alkyl.

"Alkylaryl" means an alkyl-aryl- group in which the alkyl and aryl are as previously described. Preferred alkylaryls comprise a lower alkyl group. Non-limiting examples of suitable alkylaryl groups include tolyl and xylyl. The alkylaryl is linked to an adjacent moiety through the aryl.

"Aralkenyl" means an aryl-alkenyl- group in which the aryl and alkenyl groups are as previously described. Preferred aralkenyls contain a lower alkenyl group. Non-limiting examples of suitable aralkenyl groups include phenethenyl and naphthylethenyl. The aralkenyl is linked to an adjacent moiety through the alkenyl.

"Aralkynyl" means an aryl-alkynyl- group in which the aryl and alkynyl groups are as previously described. Preferred aralkynyls contain a lower alkynyl group. The aralkynyl is linked to an adjacent moiety through the alkynyl. Non-limiting examples of suitable aralkynyl groups include phenacetylenyl and naphthylacetylenyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The aryl group is linked to an adjacent moiety through the ether oxygen.

"Aralkyloxy" means an aralkyl-O— group in which the aralkyl group is as previously described. Non-limiting examples of suitable aralkyloxy groups include benzyloxy and naphthalenemethoxy. The aralkyl group is linked to an adjacent moiety through the ether oxygen.

"Alkylamino" means an —NH$_2$ or —NH$_3^+$ group in which one or more of the hydrogen atoms on the nitrogen is replaced by an alkyl group as defined above.

"Arylamino" means an —NH$_2$ or —NH$_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio and isopropylthio. The alkyl is linked to an adjacent moiety through the sulfur.

"Arylthio" means an aryl-S— group in which the aryl group is as previously described. Non-limiting examples of suitable arylthio groups include phenylthio and naphthylthio. The aryl is linked to an adjacent moiety through the sulfur.

"Aralkylthio" means an aralkyl-S— group in which the aralkyl group is as previously described. Non-limiting example of a suitable aralkylthio group is benzylthio. The aralkyl is linked to an adjacent moiety through the sulfur.

"Alkylene" refers to an alkanediyl group commonly having free valencies on two carbon atoms. Non-limiting examples include methylene, propylene and the like.

"Arylene" is a bivalent group derived from an aromatic hydrocarbon by removal of a hydrogen atom from two ring carbon atoms. Non-limiting examples include phenylene and the like.

"Heteroarylene" is a bivalent group derived from a heterocyclic aromatic compound by removal of a hydrogen atom from two ring carbon atoms such as, for example, the bivalent group derived from pyridine, pyrrole and the like.

"Alkoxycarbonyl" means an alkyl-O—C(O)— group. Non-limiting examples of suitable alkoxycarbonyl groups include methoxycarbonyl and ethoxycarbonyl. The alkoxy is linked to an adjacent moiety through the carbonyl.

"Aryloxycarbonyl" means an aryl-O—C(O)— group. Non-limiting examples of suitable aryloxycarbonyl groups include phenoxycarbonyl and naphthoxycarbonyl. The aryloxy is linked to an adjacent moiety through the carbonyl.

"Aralkoxycarbonyl" means an aralkyl-O—C(O)— group. Non-limiting example of a suitable aralkoxycarbonyl group is benzyloxycarbonyl. The aralkoxy is linked to an adjacent moiety through the carbonyl.

"Alkylsulfonyl" means an alkyl-S(O)$_2$— group. Preferred groups are those in which the alkyl group is lower alkyl. The alkyl is linked to an adjacent moiety through the sulfonyl.

"Alkylsulfinyl" means an alkyl-S(O)— group. Preferred groups are those in which the alkyl group is lower alkyl. The alkyl is linked to an adjacent moiety through the sulfinyl.

"Arylsulfonyl" means an aryl-S(O)$_2$— group. The aryl is linked to an adjacent moiety through the sulfonyl.

"Arylsulfinyl" means an aryl-S(O)— group. The aryl is linked to an adjacent moiety through the sulfinyl.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylamino, arylamino, alkylaryl, aralkenyl, heteroaralkyl, alkylheteroaryl, heteroaralkenyl, hydroxy, hydroxyalkyl, alkoxy, aryloxy, aralkoxy, aralkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Cycloalkyl" means a non-aromatic mono- or multicyclic fused ring system comprising 3 to 24 carbon atoms, preferably 5 to 10 carbon atoms. Preferred cycloalkyl rings contain 5 to 7 ring atoms, more preferably 6 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl and the like. Non-limiting examples of suitable multicyclic cycloalkyls include bicycloalkyls such as decalinyl, norbornenyl and the like, tricycloalkyls and tetracycloalkyls.

"Cycloalkenyl" means a non-aromatic mono or multicyclic ring system comprising 3 to 10 carbon atoms, preferably 5 to 10 carbon atoms which contains at least one carbon-carbon double bond. Preferred cycloalkenyl rings contain 5 to 7 ring atoms, more preferably 6 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornenyl.

"Acyl" means an H—C(O)—, alkyl-C(O)—, alkenyl-C(O)—, aryl-C(O)—, heteroaryl-C(O)—, alkynyl-C(O)—, cycloalkyl-C(O)—, cycloalkenyl-C(O)—, or cycloalkynyl-C(O)— group in which the various groups are as previously described. The bond to the parent moiety is through the carbon atom of the carbonyl. Non-limiting examples of suitable acyl groups include formyl, acetyl, propanoyl, 2-methylpropanoyl, butanoyl, benzoyl and cyclohexanoyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Heteroaryl" represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. Preferred heteroaryls contain 5 to 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. Nitrogen atoms can form an N-oxide. All regioisomers are contemplated, e.g., 2-pyridyl, 3-pyridyl and 4-pyridyl. Useful 6-membered heteroaryl groups include pyridyl, pyrimidinyl, pyrazinyl, pyridazinyl and the like and the N-oxides thereof. Useful 5-membered heteroaryl rings include furyl, thienyl, pyrrolyl, thiazolyl, isothiazolyl, imidazolyl, pyrazolyl, isoxazolyl and the like. Useful bicyclic groups include benzo-fused ring systems derived from the heteroaryl groups named above, e.g. quinolyl, phthalazinyl, quinazolinyl, benzofuranyl, benzothienyl, indolyl and the like.

"Alkylene" refers to an alkanediyl group commonly having free valencies on two carbon atoms. Non-limiting examples include ethylene, propylene and the like.

"Alkoxy" means an alkyl radical attached by an oxygen, i.e., alkyl-O—, wherein the alkyl is 1 to 9 carbon atoms. Non-limiting examples of alkoxy groups include methoxy, ethoxy, n-propoxy, isopropoxy, n-butoxy, t-butoxy, n-pentoxy, and heptoxy.

"Haloalkyl" means alkyl having one or more halo atom substituents. Non-limiting examples include —CH$_2$Cl, —CHCl$_2$, —CCl$_3$, —CH$_2$F, —CHF$_2$, —CF$_3$, —CH$_2$—CH$_2$Cl, —CH$_2$—CHCl$_2$, and —CHCl—CH$_2$Cl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl optionally substituted with 1 to 5 R$^3$ groups.

"Patient" includes humans, other mammals and other animals.

"Mammal" includes humans and other mammalian animals.

The term "pharmaceutically effective amount" is intended to mean an amount of a therapeutic agent that will have the desired effect on a tissue, system, animal or mammal that is being sought by the administrator (such as a researcher, doctor or veterinarian), which includes alleviation of the symptoms of the condition or disease being treated and the prevention, slowing or halting of progression of the disease, for example, the cognitive neurodegenerative disease(s) such as Alzheimer's disease and senile dementia, with treatment resulting in improvement in memory and learning.

Nitrogen protecting group (Prot) means a group capable of protecting a nitrogen from a reaction. Preferred nitrogen protecting groups are carbobenzyloxy (CBz), $CH_3OCO(CH_2)_9CO$, and t-butoxycarbonyl (BOC). Other useful operable nitrogen protecting groups would be well known to those skilled in the art.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association may involve varying degrees of ionic and covalent bonding, including hydrogen bonding. In certain instances the solvate may be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of formula I can form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfoirates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; and Anderson et al, *The Practice of Medicinal Chemistry* (1996), Academic Press, New York). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate, and prodrug of enantiomers, stereoisomers, rotamers, tautomers, racemates or prod rugs of the inventive compounds.

Another aspect of the invention relates to a pharmaceutical composition which comprises at least one compound having structural formula I, preferably in combination with at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Another aspect of the invention relates to a method of making a pharmaceutical composition comprising contacting at least one compound of formula I with at least one pharmaceutically acceptable carrier described above.

Another aspect of the invention relates to a method of treating a cognitive or neurodegenerative disease comprising administering to a patient suffering from said disease at least one compound of formula I. Preferably, the amount of compound of formula I administered is a pharmaceutically effective amount. The amount compound of formula I administered to a patient can be from about 0.0001 to about 40 mg/kg of body weight, preferably from about 0.001 to about 20 mg/kg, and more preferably from about 0.005 to about 10 mg/kg of body weight.

Modes of administration include, but are not limited to, oral, parenteral and transdermal. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it can be the appropriate number of any of these in a packaged form.

The dosages and frequency of administration of the compound having formula I and/or the pharmaceutically acceptable salts or solvates thereof can be regulated according to the judgement of the attending clinician considering such factors as age, condition and size of the patient as well as severity of the symptoms being treated. For convenience, the total daily dosage can be divided and administered in portions throughout the day or by means providing continuous delivery.

Another aspect of the invention relates to a method of treating a cognitive or neurodegenerative disease comprising administering to a patient suffering from said disease at least one compound of formula I in association with at least one acetylcholinesterase inhibitor. Preferably the amount of compound of formula I and the amount of inhibitor administered is a pharmaceutically effective amount. The amount of compound of formula I and the amount of inhibitor administered to a patient can each be independently from about 0.001 to about 100 mg/kg of body weight, preferably from about 0.005 to about 40 mg/kg of body weight, and more preferably from about 0.01 to about 20 mg/kg of body weight.

When a compound of formula I is used in association with an acetylcholinesterase inhibitor to treat cognitive disorders, these two active components can be co-administered simultaneously or sequentially, or a single pharmaceutical composition comprising a compound of formula I and an acetylcholinesterase inhibitor in a pharmaceutically acceptable carrier can be administered. The association of the compound of formula I and the inhibitor means the compound and inhibitor can be administered individually or together in any conventional oral or parenteral dosage form such as capsule, tablet, powder, cachet, suspension, solution, suppository, nasal spray, etc. The dosage of the acetylcholinesterase inhibitor can range from about 0.001 to about 100 mg/kg body weight.

Another aspect of the invention relates to a kit for treating a cognitive or neurodegenerative disease comprising in a single package a first container and a second container for use in combination, said first container comprising at least one compound of formula I and said second container comprising at least one acetylcholinesterase inhibitor, said compound and inhibitor each preferably being in a pharmaceutically acceptable carrier. Preferably, the quantities of the compound and inhibitor is a pharmaceutically effective amount. The amount compound of formula I and inhibitor administered to a patient can each be from about 0.0001 to about 40 mg/kg, preferably from about 0.001 to about 20 mg/kg, and more preferably from about 0.005 to about 10 mg/kg.

The following abbreviations are used in the procedures and schemes:

Aqueous (aq), trifluoroacetic anhydride (TFAA), trifluoracetic acid (TFA), 4-dimethylaminopyridine (DMAP), 1-(3-dimethylaminopropyl-3-ethylcarbodiimide (EDCI), and tetrabutylammonium bromide (TBAB).

Compounds in accordance with formula I can be produced by processes known to those skilled in the art as shown by the following reaction steps:

General Description of Methods

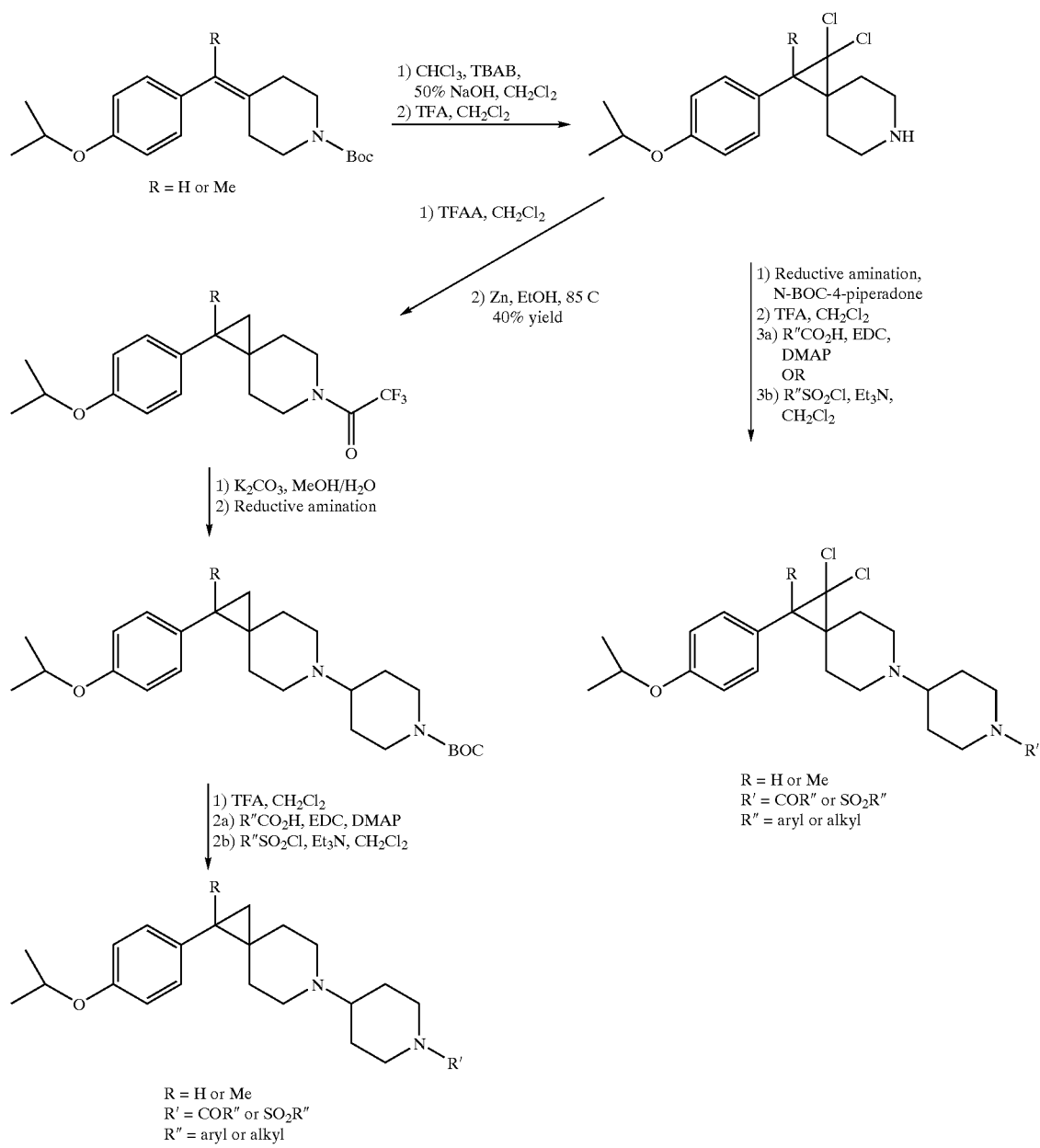

The above reactions can be followed if necessary or desired by one or more of the following steps: (a) removing any protective groups from the compound so produced; (b) converting the compound so-produced to a pharmaceutically acceptable salt, ester and/or solvate, and (c) isolating a compound of formula I, including separating stereoisomers of formula I.

Based on the foregoing reaction sequence, those skilled in the art will be able to select starting materials needed to produce the compound in accordance with formula I.

In the above processes it may be sometimes desirable and/or necessary to protect certain groups during the reactions. Conventional protecting groups, familiar to those skilled in the art, can be used. After the reaction or reactions, the protecting groups can be removed by standard procedures.

The invention disclosed herein is exemplified by the following preparation and examples which should not be construed to limit the scope of the disclosure. Alternative mechanistic pathways and analogous structures can be apparent to those skilled in the art.

EXAMPLES

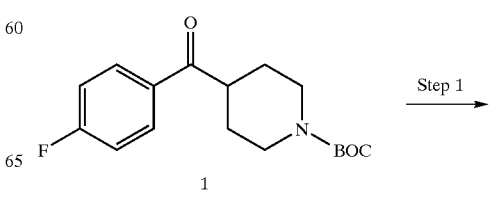

Step 1

-continued

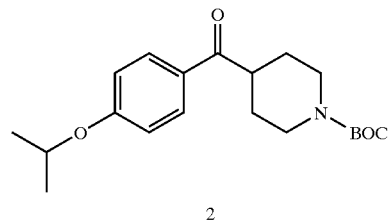

2

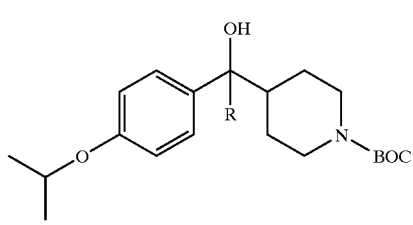

3a: R = H
3b: R = Me

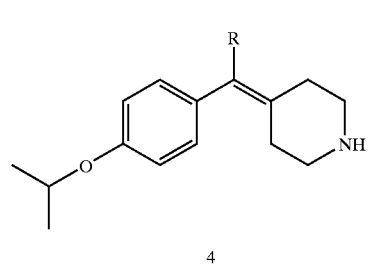

4

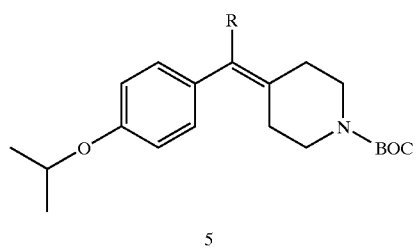

5

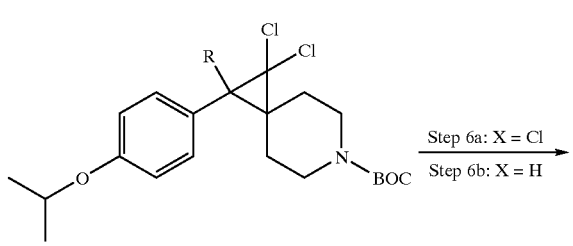

6

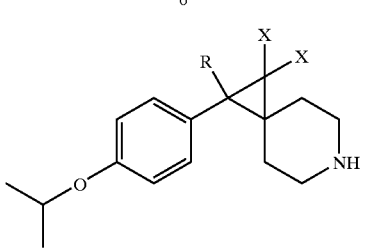

7a: X = Cl
7b: X = H

Step 2a: R = H
Step 2b: R = Me

Step 3

Step 4

Step 5

Step 6a: X = Cl
Step 6b: X = H

Step 7

-continued

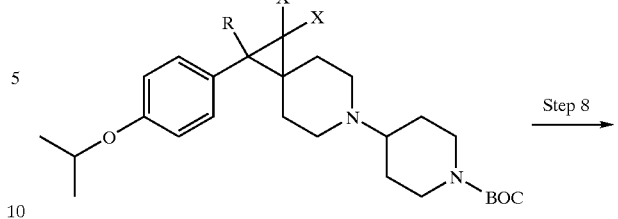

8

Step 8

Step 9a: R' = COR''
Step 9b: R' = SO₂R''

9

10a: R' = COR''
10b: R' = SO₂R''

Step 1: Isopropanol (1.64 g, 65.1 mmol) was added dropwise over 35 minutes to a suspension of sodium hydride (1.64 g, 65.1 mmol) and 1-methyl-2-pyrrolidine (75 mL) under a nitrogen atmosphere. The reaction mixture was heated to 80° C. for 30 minutes. The reaction mixture was cooled to room temperature, compound 1 (10.0 g, 32.5 mmol) was added, and the reaction was heated to 60° C. After 16 hours, the reaction mixture was poured onto 1 N NaOH (200 mL), stirred for 30 minutes and extracted with ether. The combined organics were washed with 1 N NaOH, dried over magnesium sulfate, then filtered and concentrated under reduced pressure.

Purification via flash chromatography (20% ethyl acetate/hexanes) yielded the desired product 2 (6.04 g, 17.4 mmol, 53% yield). HRMS (FAB$^+$): Calcd for $C_{20}H_{30}NO_4$ (M+H)$^+$: 348.2175. Found: 348.2078.

Step 2a: Sodium borohydride (0.26 g, 6.9 mmol) was added slowly to a solution of the ketone 2 (2.00 g, 5.76 mmol) in ethanol (95%, 58 mL) at 0° C. (ice bath). The reaction mixture was warmed to room temperature and stirred for 16 hours. The reaction mixture was then quenched with sat'd NH$_4$Cl and extracted with dichloromethane. The combined organics were dried over magnesium sulfate, filtered and concentrated under reduced pressure to give the desired product 3a (2.01 g, 5.76 mmol), which was used without further purification in the next reaction.

Step 2b: Methyl magnesium bromide (3M in THF, 4.1 mL, 12.3 mmol) was added slowly to a solution of the ketone 2 (2.00 g, 5.76 mmol) in tetrahydrofuran (29 mL) at 0° C. (ice bath) under a nitrogen atmosphere. The reaction was warmed to room temperature and stirred for 16 hours. The reaction mixture was quenched with sat'd NH$_4$Cl and extracted with ethyl acetate. The combined organics were washed with brine, dried over magnesium sulfate, and filtered and concentrated under reduced pressure to give the desired product 3b (2.06 g, 5.67 mmol), which was used without further purification.

Step 3: p-Toluenesulfonic acid (1.30 g, 6.83 mmol) was added to a solution of the alcohol 3a or 3b (2.01 g, 5.76 mmol) in toluene (58 mL) and heated to reflux. After 6 hours, the reaction was quenched with 1 N NaOH and extracted with dichloromethane. The combined organics were dried over potassium carbonate, filtered and concentrated under reduced pressure to give the desired product 4 (1.33 g, 5.76 mmol), which was used in the next reaction without further purification.

Step 4: To a solution of the amine 4 (1.33 g, 5.76 mmol) in dichloromethane (58 mL) was added a solution of di-t-butyl dicarbonate (1.46 g, 6.69 mmol) in dichloromethane (10 mL). After 1 hour, the reaction mixture was quenched with water and extracted with dichloromethane. The combined organics were dried over potassium carbonate, filtered and concentrated under reduced pressure. Purification via flash chromatography (20% ethyl acetate/hexanes) yielded the desired product 5 (1.82 g, 5.49 mmol, 95%).

Step 5: Tetrabutylammonium bromide (30 mg, 0.13 mmol) was added to a mixture of the alkene 5 (0.71 g, 2.14 mmol) in chloroform (10 mL) and 50% aqueous sodium hydroxide (2 mL). The reaction was flushed with nitrogen and stirred at ambient temperature in a sealed tube. After 16 hours, the reaction mixture was diluted with dichloromethane and washed with water. The aqueous layer was extracted with dichloromethane and the combined organics were dried over magnesium sulfate, filtered and concentrated under reduced pressure. Purification via flash chromatography (5% to 10% ethyl acetate/hexanes) yielded the desired product 6 (0.87 g, 2.14 mmol, 100%). HRMS (FAB$^+$): Calcd for $C_{21}H_{30}Cl_2NO_3$ (M+H)$^+$: 413.1524. Found: 413.1538.

Step 6a: Trifluoroacetic acid (2.8 mL, 3.6 mmol) was added to a solution of compound 6 (0.99 g, 2.4 mmol) in dichloromethane (24 mL) under a nitrogen atmosphere and stirred at ambient temperature. After 30 minutes, the reaction mixture was diluted with dichloromethane, washed with 1 N NaOH. The aqueous layer was extracted with dichloromethane and the combined organics were dried over potassium carbonate, filtered and concentrated under reduced pressure to give the free amine 7a (0.75 g, 2.4 mmol) which was used in the following reaction without further purification.

Step 6b: Following step 6a, trifluoroacetic anhydride (0.10 mL, 0.72 mmol) was added to a solution of compound 7a (0.17 g, 0.55 mmol) in dichloromethane (6 mL) under a nitrogen atmosphere and stirred at ambient temperature. After 1.5 hours, the reaction mixture was diluted with dichloromethane, and washed with 1 N NaOH. The aqueous layer was extracted with dichloromethane and the combined organics were dried over potassium carbonate, filtered and concentrated under reduced pressure. Purification via PTLC (10% ethyl acetate/hexanes) yielded the trifluoroacetamide (0.21 g, 0.81 mmol, 88%).

Zinc dust (0.29 g, 4.40 mmol) was added to a solution of the trifluoroacetamide (0.21 g, 0.81 mmol) in ethanol (5 mL) and water (0.5 mL) under a nitrogen atmosphere, then heated to 84° C. for 21 hours. The zinc was filtered off and washed with 10% HCl followed by dichloromethane. The mixture was extracted with dichloromethane and the combined organics were dried over potassium carbonate, filtered and concentrated under reduced pressure. The crude material (202 mg) was dissolved in dichloromethane (5 mL) and trifluoroacetic anhydride (0.07 ml) was added under a nitrogen atmosphere and stirred at ambient temperature. After 16 hours, the reaction mixture was diluted with dichloromethane and washed with 1 N NaOH. The aqueous layer was extracted with dichloromethane and the combined organics were dried over potassium carbonate, filtered and concentrated under reduced pressure. Purification via PTLC (10% ethyl acetate/hexanes, developed 3 times) yielded the desired product (0.07 g, 0.21 mmol, 40%). HRMS (FAB$^+$): Calcd for $C_{18}H_{23}NO_2$ (M+H)$^+$: 342.1674. Found: 342.1681.

Potassium carbonate (0.05, 0.41 mmol) was added to a solution of the des-chloro compound (0.07 g, 0.21 mmol) in methanol (2 mL) and water (1 mL) and the reaction was stirred at ambient temperature. After 1 hour, the reaction mixture was diluted with dichloromethane and washed with 1 N NaOH. The aqueous layer was extracted with dichloromethane and the combined organics were dried over potassium carbonate, filtered and concentrated under reduced pressure to give the desired product 7b (0.05 g, 0.21 mmol) which was used without further purification.

Step 7: To a solution of the amine 7a or 7b (0.75, 2.40 mmol) in dichloromethane (8 mL) was added the ketone N-BOC-4-piperidone (574 mg, 2.88 mmol), sodium triacetoxyborohydride (710 mg, 3.35 mmol) and acetic acid (0.13 mL, 2.40 mmol). After stirring at room temperature for 20 hours, the reaction mixture was diluted with dichloromethane and washed with 1 N NaOH. The organic layer was dried over potassium carbonate, filtered and concentrated under reduced pressure. Purification via flash chromatography (3% methanol/dichloromethane) yielded the desired product 8 (0.40 g, 0.81 mmol, 34%). HRMS (FAB$^+$): Calcd for $C_{26}H_{39}Cl_2N_2O_3$ (M+H)$^+$: 499.2308. Found: 499.2303.

Step 8: Trifluoroacetic acid (0.95 mL, 1.2 mmol) was added to a solution of compound 8 (0.40 g, 0.81 mmol) in dichloromethane (8 mL) under a nitrogen atmosphere and stirred at ambient temperature. After 2 hours, the reaction mixture was diluted with dichloromethane and washed with 1 N NaOH. The aqueous layer was extracted with dichloromethane and the combined organics were dried over potassium carbonate, filtered and concentrated under reduced pressure to give the desired product 9 (0.30 g, 0.76 mmol, 95%) which was used in the next reaction without further purification.

Step 9a: To a mixture of the corresponding acid which are listed below (0.08 mmol), EDCI (0.09 mmol) and DMAP (0.06 mmol) was added compound 9 (0.06 mmol) in dichloromethane (0.6 mL). The reaction mixture was flushed with nitrogen and stirred in a sealed tube at ambient temperature. After 21 hours, the reaction was diluted with dichloromethane and washed with 1 N NaOH, dried over potassium carbonate, filtered and concentrated under reduced pressure. Purification via PTLC (5% methanol/dichloromethane) yielded the desired product 10a (0.06 mmol).

Step 9b: The corresponding sulfonyl chloride (0.05 mmol) was added to a solution of 9 (0.05 mmol) in dichloromethane (0.6 mL) and triethylamine (0.05 mmol) under a nitrogen atmosphere and stirred at ambient temperature. After 16 hours, the reaction mixture was diluted with dichloromethane and washed with water. The organics were dried over potassium carbonate, filtered and concentrated under reduced pressure. Purification via PTLC (5% methanol/dichloromethane) yielded the desired product 10b (0.04 mmol).

Synthesis of Compound 1:

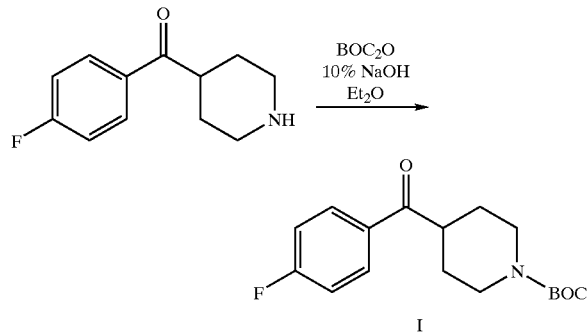

4-(4-Fluorobenzoyl)piperidine hydrochloride (25.0 g, 103 mmol, Oakwood Products, Inc.; 1741 Old Dunbar Rd.; West Columbia, S.C., 29172) was dissolved in $Et_2O$ (125 mL) and 10% NaOH (125 mL) and cooled to 0 C with vigorous stirring. A solution of $BOC_2O$ (26.9 g, 123 mmol) in $Et_2O$ was added dropwise over 30 min. After stirring at rt for 2 h, the mixture was poured into a separatory funnel and extracted with $Et_2O$. The organics were washed with brine, dried over $MgSO4$, filtered, and concentrated under reduced pressure. Compound 1 was obtained in quantitative yield (31.5 g, 103 mmol).

For Compound No. 1 in the Table of Compounds, 2-chloro-3-methylbenzoic acid was used in step 9a as the corresponding acid.

HRMS ($FAB^+$): Calcd for $C_{29}H_{36}Cl_3N_2O_2$ $(M+H)^+$: 549.1842. Found: 549.1835.

For compound Nos. 2, 7 and 12, in the Table of Compounds, 3-chloro-2-methylbenzoic acid was used in step 9a as the corresponding acid.

HRMS ($FAB^+$): For compound No. 2: Calcd for $C_{29}H_{36}Cl_3N_2O_2$ $(M+H)^+$: 549.1842.

Found: 549.1848. For compound No. 7: Calcd for $C_{29}H_{38}ClN_2O_2$ $(M+H)^+$: 481.2622.

Found: 481.2616. For compound No. 12: Calcd for $C_{30}H_{40}ClN_2O_2$ $(M+H)^+$: 495.2778.

Found: 495.2762.

For compound Nos. 3, 8 and 10 in the Table of Compounds, 2,3-dichlorobenzoic acid was used in step 9a as the corresponding acid.

HRMS ($FAB^+$): For compound No. 3: Calcd for $C_{28}H_{33}Cl_4N_2O_2$ $(M+H)^+$: 571.1267.

Found: 571.1270. For compound No. 8: Calcd for $C_{28}H_{35}Cl_2N_2O_2$ $(M+H)^+$: 501.2076.

Found: 501.2069. For compound No. 10: Calcd for $C_{29}H_{37}Cl_2N_2O_2$ $(M+H)^+$: 515.2232.

Found: 515.2233.

For compound No. 4 in the Table of Compounds, 2-amino-3-methylbenzoic acid was used in step 9a as the corresponding acid.

HRMS ($FAB^+$): Calcd for $C_{29}H_{38}Cl_2N_3O_2$ $(M+H)^+$: 530.2341. Found: 530.2348.

For compound Nos. 5, 9 and 11 in the Table of Compounds, 2-amino-3-chlorobenzoic acid was used in step 9a as the corresponding acid.

HRMS ($FAB^+$): For compound No. 5: Calcd for $C_{28}H_{35}Cl_3N_3O_2$ $(M+H)^+$: 550.1795.

Found: 550.1790. For compound No. 9: Calcd for $C_{28}H_{37}ClN_3O_2$ $(M+H)^+$: 482.2574.

Found: 482.2570. For compound No. 11: Calcd for $C_{29}H_{39}ClN_3O_2$ $(M+H)^+$: 496.2718.

Found: 496.2731.

For compound No. 6 in the Table of Compounds, 2-amino-3-fluorobenzoic acid was used in step 9a as the corresponding acid.

HRMS ($FAB^+$): Calcd for $C_{28}H_{35}Cl_2FN_3O_2$ $(M+H)^+$: 534.2090. Found: 534.2074.

For compound No. 13 in the Table of Compounds, 4-fluoro-1-naphthoic acid was used in step 9a as the corresponding acid.

HRMS (FAB): Calcd for $C_{32}H_{36}Cl_2FN_2O_2$ $(M+H)^+$: 569.2138. Found: 569.2125.

For compound No. 14 in the Table of Compounds, 5-bromo-1-naphthoic acid was used in step 9a as the corresponding acid.

HRMS (FAB): Calcd for $C_{32}H_{36}BrCl_2N_2O_2$ $(M+H)^+$: 631.1317. Found: 631.1331.

For compound No. 15 in the Table of Compounds, n-propylsulfonyl chloride was used in step 9b as the corresponding sulfonyl chloride.

HRMS (FAB): Calcd for $C_{24}H_{37}Cl_2N_2O_3S$ $(M+H)^+$: 503.1902. Found: 503.1904.

For compound No. 16 in the Table of Compounds, 1-naphthylsulfonyl chloride was used in step 9b as the corresponding sulfonyl chloride.

HRMS (FAB): Calcd for $C_{31}H_{37}Cl_2N_2O_3S$ $(M+H)^+$: 587.1902. Found: 587.1897.

For compound No. 17 in the Table of Compounds, 2-6-dimethylbenzoic acid was used in step 9b as the corresponding acid HRMS (FAB): Calcd for $C_{30}H_{39}Cl_2N_2O_2$ $(M+H)^+$: 529.2389. Found: 529.2397.

Using the appropriate starting materials in the procedures described above or modifications of those procedures well known to those skilled in the art, the compounds shown in the following table were prepared.

TABLE OF COMPOUNDS
| COMPOUND No. | STRUCTURE |
| --- | --- |
| 1 | 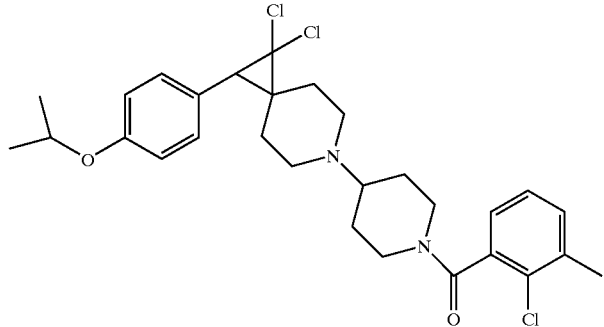 |
| 2 | 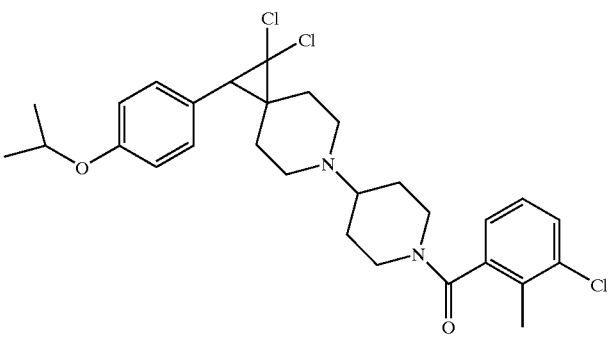 |
| 3 | 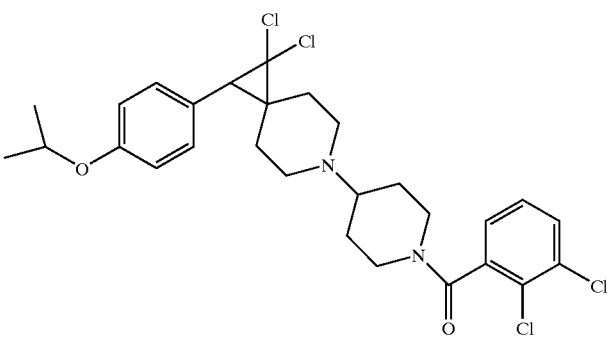 |
| 4 | 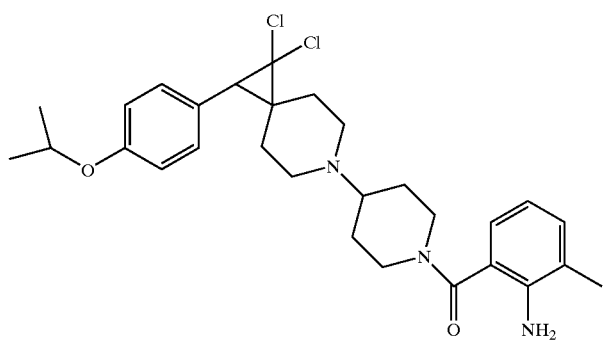 |

-continued
TABLE OF COMPOUNDS
| COMPOUND No. | STRUCTURE |
| --- | --- |
| 5 | 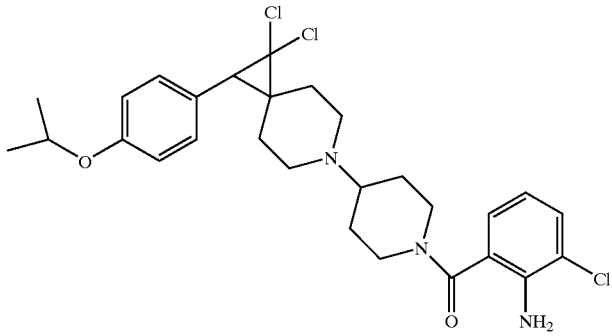 |
| 6 | 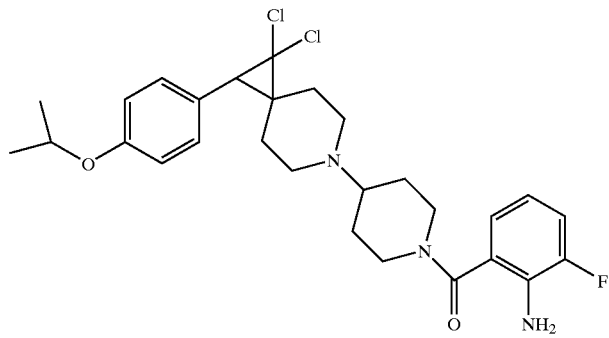 |
| 7 | 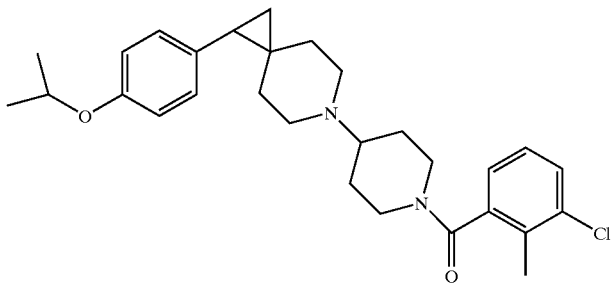 |
| 8 | 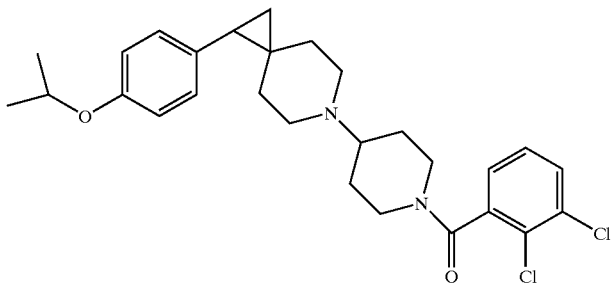 |

-continued
TABLE OF COMPOUNDS
| COMPOUND No. | STRUCTURE |
|---|---|
| 9 | 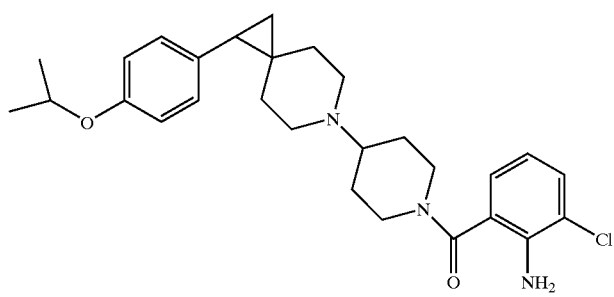 |
| 10 | 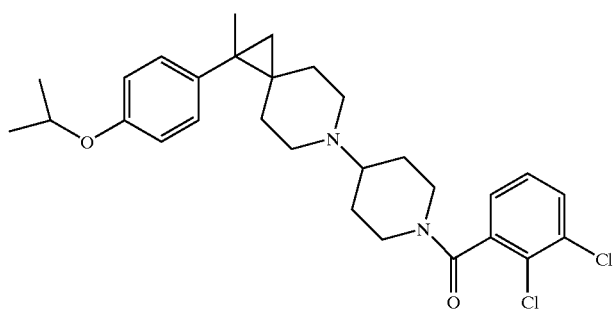 |
| 11 | 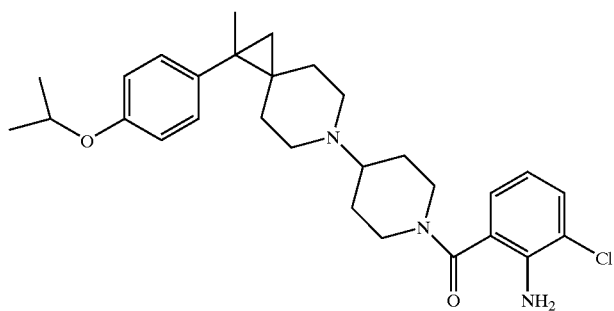 |
| 12 | 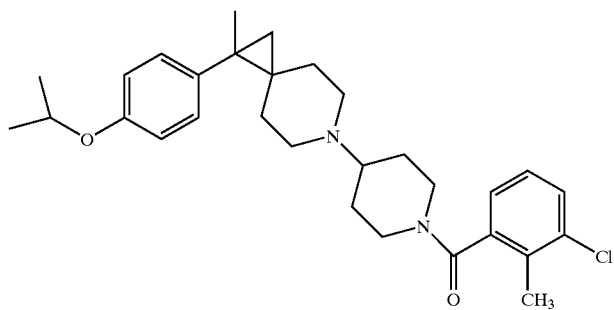 |

-continued
TABLE OF COMPOUNDS
| COMPOUND No. | STRUCTURE |
|---|---|
| 13 | 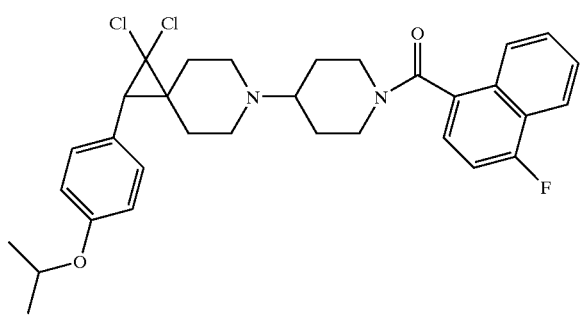 |
| 14 | 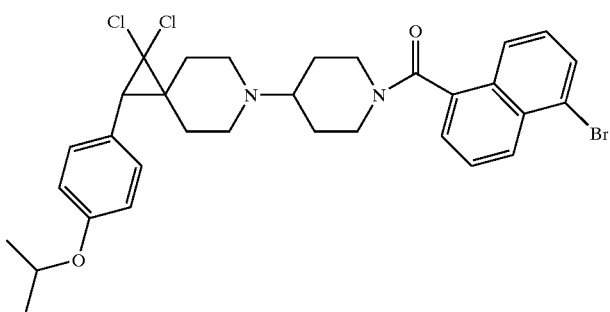 |
| 15 | 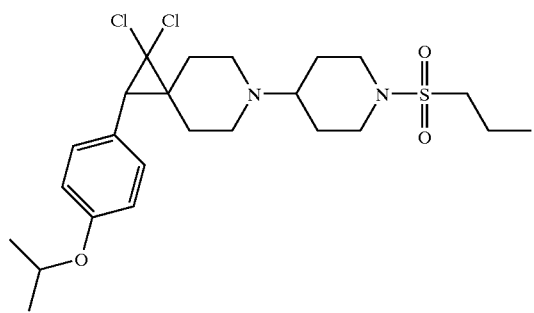 |
| 16 | 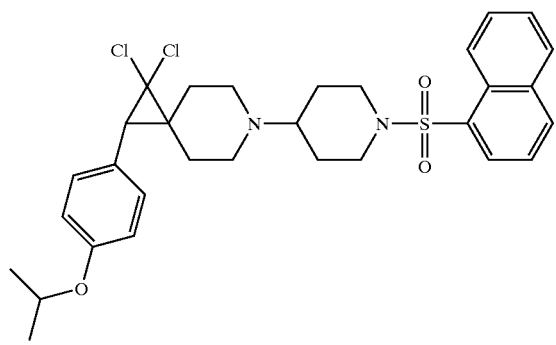 |

-continued

TABLE OF COMPOUNDS

| COMPOUND No. | STRUCTURE |
|---|---|
| 17 | 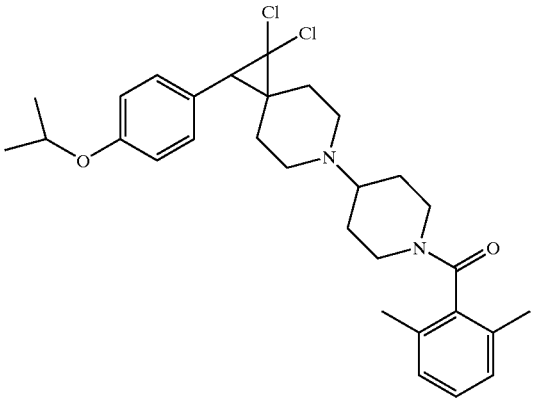 |

The compounds of formula I can exhibit selective $M_2$ and/or $M_4$ muscarinic antagonizing activity, which has been correlated with pharmaceutical activity for treating cognitive disorders such as Alzheimer's disease and senile dementia.

The compounds of formula I display pharmacological activity in test procedures designated to indicate muscarinic antagonist activity. Following are descriptions of the test procedures.

Muscarinic Binding Activity

The compounds of interest were tested for their ability to inhibit binding to the cloned human $M_1$, $M_2$, $M_3$, $M_4$ and $M_5$ muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homogenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., "[3H]pipernzepine and (−)-[3H]quinuclidinyl benzilate binding to rat cerebral cortical and cardiac muscarinic cholinergic sites. I. Characterization and regulation of agonist binding to putative muscarinic subtypes." J. Pharmacol. Exp. Ther., 1986, May; 237(2):411–8). Briefly, membranes (approximately 8, 20, and 14 μg of protein assay for the $M_1$, $M_2$, $M_3$, $M_4$ and $M_5$ containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, G. A. Kinetic, EBDA, Ligand, Lowry: A Collection of Radioligand Binding Analysis Programs. Elsevier Science Publishers BV, Amsterdam, 1985). Affinity values ($K_i$) were then determined using the following formula [Y-C. Cheng and W. H. Prusoff, "Relationship between the inhibitory constant (Ki) and the concentration of inhibitor which causes 50 percent inhibition ($IC_{50}$) of an enzymatic reaction," Biochem. Pharmacol. 22 (1973) 3099–3108].

$$K_i = \frac{IC_{50}}{1 + \left[\frac{\text{concentration of radioligand}}{\text{affinity } (K_D) \text{ of radioligand}}\right]}$$

Hence, a lower value of $K_i$ indicates greater binding affinity.

To determine the degree of selectivity of a compound for binding to a particular muscarinic receptor, the $K_i$ value of a first muscarinic receptor is divided by the $K_i$ value of another muscarinic receptor. For example, when the $K_i$ value of the $M_1$ receptors is divided by the $K_i$ value of the $M_2$ receptors, a higher ratio indicates a greater selectivity for binding to the $M_2$ muscarinic receptor.

RESULTS OF THE TESTS

| Compound No. | Ki (nM) | | | | |
|---|---|---|---|---|---|
| | $M_1$ | $M_2$ | $M_3$ | $M_4$ | $M_5$ |
| 1 | >990 | >1400 | >1000 | >1000 | 891 |
| 2 | 982 | >1400 | | | |
| 3 | >996 | >1440 | >1000 | >1000 | >1500 |
| 4 | >990 | 77 | >1000 | >1000 | 96 |
| 5 | >990 | 1393 | >1000 | >1000 | 786 |
| 6 | >990 | 1200 | >1000 | >1000 | 42 |
| 7 | >900 | >1377 | >1000 | >1000 | >1500 |
| 8 | 819 | 607 | >1000 | >1000 | >1500 |
| 9 | >900 | 490 | >1000 | >1000 | >1500 |
| 10 | 1013 | 149 | >1200 | 261 | 995 |
| 11 | 600 | 49 | 691 | 151 | 619 |
| 12 | 744 | 113 | >1200 | 272 | 1210 |

-continued

RESULTS OF THE TESTS

| Compound No. | Ki (nM) | | | | |
|---|---|---|---|---|---|
| | $M_1$ | $M_2$ | $M_3$ | $M_4$ | $M_5$ |
| 13 | >1200 | >1900 | — | — | — |
| 14 | >1200 | >1900 | — | — | — |
| 15 | >1200 | 481 | — | — | — |
| 16 | >1200 | 1836 | — | — | — |
| 17 | >1200 | >1900 | — | — | — |

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

We claim:

1. A compound having the structural formula (I):

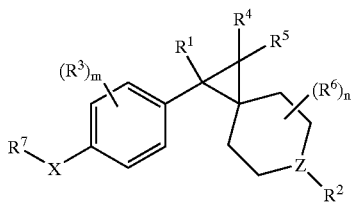

(I)

or pharmaceutically acceptable salts or solvates thereof; wherein:

$R^1$ is selected from the group consisting of H alkyl, alkenyl and alkynyl;

$R^2$ is

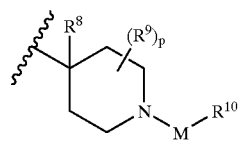

p is 0–4;
m is 0–4;
n is 0–4;

$R^3$ is selected from the group consisting of H, alkyl, halo, alkoxy, hydroxy, nitro, aminoalkyl, and acyl, wherein $R^3$ can be the same or different and is independently selected when m is 2–4;

$R^4$ and $R^5$, which can be the same or different, are each independently selected from the group consisting of H and halogen;

$R^6$ is selected from the group consisting of H, halo, alkyl, hydroxy, hydroxyalkyl, arylalkyl, aminoalkyl, haloalkyl, and thioalkyl, wherein $R^6$ can be the same or different and is independently selected when n is 2–4;

$R^7$ is selected from the group consisting of hydrogen, acyl, alkyl, alkoxy, alkenyl, cycloalkyl, cycloalkyl substituted with 0–2 alkyl groups which can be the same or different and are independently selected, cycloalkenyl, bicycloalkyl, arylalkenyl and arylalkyl;

$R^8$ is selected from the group consisting of H, alkyl, aryl, heteroaryl, halo, and cycloalkyl;

$R^9$ is selected from the group consisting of H, alkyl, aryl, halo, hydroxy and cycloalkyl, wherein $R^9$ can be the same or different and is independently selected when (p) is 2–4, or two $R^9$ groups can be joined together to form the group —$(CH_2)_r$—, wherein r is 1 to 6;

$R^{10}$ is selected from the group consisting of substituted or unsubstituted alkyl, substituted or unsubstituted aryl, and substituted or unsubstituted heteroaryl, with the proviso that when $R^{10}$ is a substituted or unsubstituted heteroaryl, the bond to M is from a carbon atom in the $R^{10}$ group;

Z is N;

X is selected from the group consisting of —O—, —S—, —S(O)—, —S(O)$_2$—, —C(O)—, -alkylene-, —C(S)—, —C(alkyl)$_2$- and —C(H)(alkyl)-; and M is —S(O)$_2$— or —C(O)—.

2. The compound according to claim 1, wherein $R^7$ is —CH(CH$_3$)$_2$.

3. The compound according to claim 1, wherein $R^3$ is H.

4. The compound according to claim 1, wherein $R^6$ is H.

5. The compound according to claim 1, wherein $R^1$ is H or methyl.

6. The compound according to claim 1, wherein X is —O—.

7. The compound according to claim 1, wherein $R^8$ is H.

8. The compound according to claim 1, wherein $R^9$ is H.

9. The compound according to claim 1, wherein $R^{10}$ is a substituted or unsubstituted alkyl, or a substituted or unsubstituted aryl.

10. The compound according to claim 9, wherein $R^{10}$ is a substituted aryl.

11. The compound according to claim 10, wherein said substituted aryl is substituted with one or more groups selected from the group consisting of alkyl, halogen and amino.

12. The compound according to claim 1, wherein the compound of formula I is:

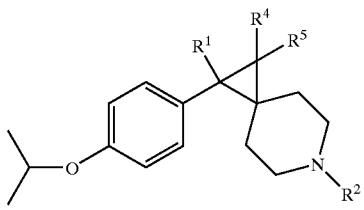

and wherein $R^1$, $R^2$, $R^4$ and $R^5$ are defined in the following table for the compounds shown:

| Compound # | $R^1$ | $R^2$ | $R^4$ | $R^5$ |
|---|---|---|---|---|
| 1 | H | 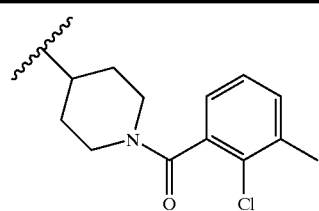 | Cl | Cl |

-continued
| Compound # | R¹ | R² | R⁴ | R⁵ |
|---|---|---|---|---|
| 2 | H | 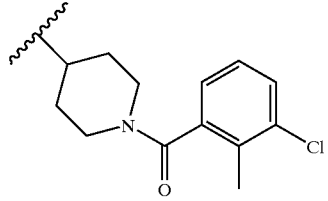 | Cl | Cl |
| 3 | H | 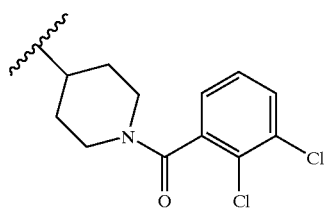 | Cl | Cl |
| 4 | H | 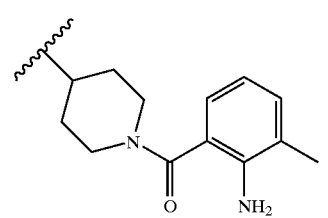 | Cl | Cl |
| 5 | H | 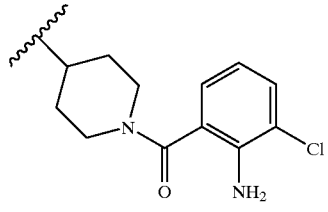 | Cl | Cl |
| 6 | H | 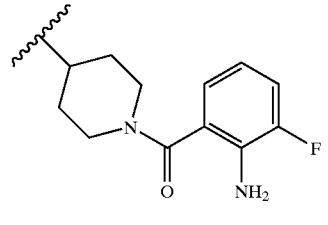 | Cl | Cl |
| 7 | H | 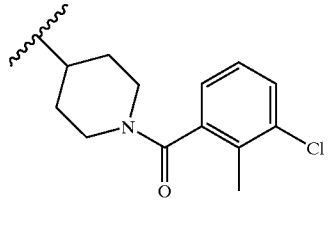 | H | H |
| 8 | H | 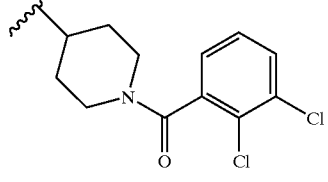 | H | H |
-continued
| Compound # | R¹ | R² | R⁴ | R⁵ |
|---|---|---|---|---|
| 9 | H | 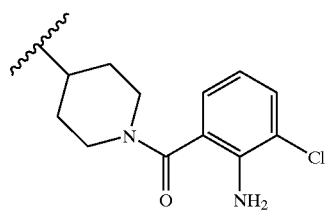 | H | H |
| 10 | CH₃ | 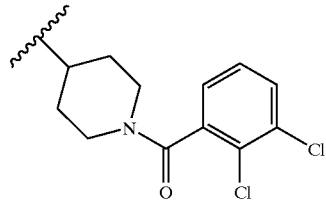 | H | H |
| 11 | CH₃ | 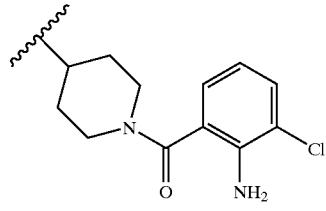 | H | H |
| 12 | CH₃ | 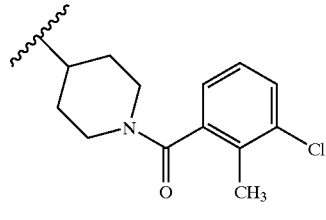 | H | H |
| 13 | H | 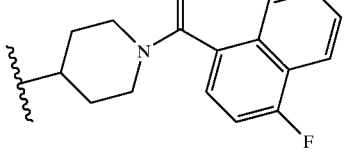 | Cl | Cl |
| 14 | H | 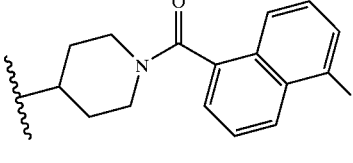 | Cl | Cl |
| 15 | H | 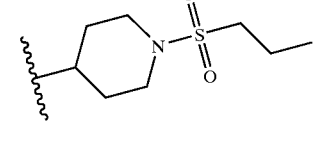 | Cl | Cl |

-continued

| Compound # | R¹ | R² | R⁴ | R⁵ |
|---|---|---|---|---|
| 16 | H | 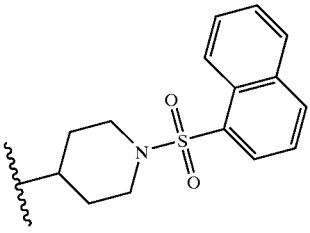 | Cl | Cl |
| 17 | H |  | Cl | Cl |

13. The compound according to claim 1 having the following formula:

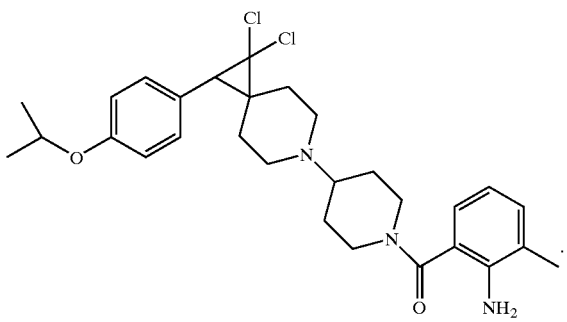

14. The compound according to claim 1 having the following formula:

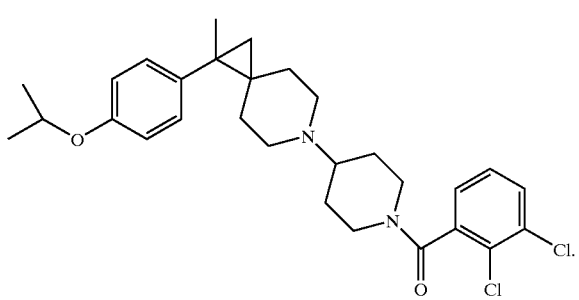

15. The compound according to claim 1 having the following formula:

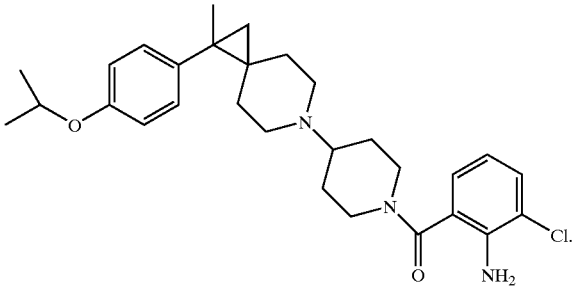

16. The compound according to claim 1 having the following formula:

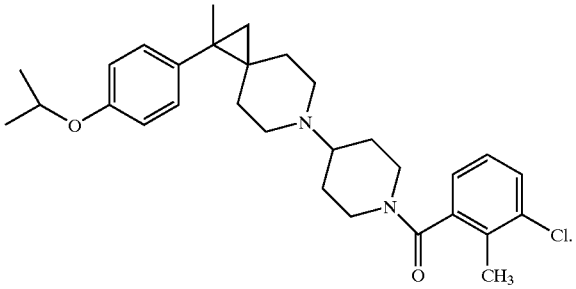

17. A pharmaceutical composition consisting of at least one compound according to claim 1.

18. The pharmaceutical composition according to claim 17, further comprising at least one pharmaceutically acceptable carrier.

19. A method of making the pharmaceutical composition according to claim 18 comprising mixing at least one compound according to claim 1 with at least one pharmaceutically acceptable carrier.

20. A method of treating Senile Dementia or Alzheimer's disease comprising administering to a patient suffering from said disease at least one compound according to claim 1.

21. The method of treating Senile Dementia or Alzheimer's disease according to claim 20, wherein the amount of compound of formula I administered is a therapeutically effective amount for treatment of the cognitive or neurological disease.

22. The method of treating Senile Dementia or Alzheimer's disease according to claim 21, wherein the amount of compound of formula I administered is from about 0.00001 mg/kg to about 40 mg/kg of body weight.

23. The method of treating Senile Dementia or Alzheimer's disease according to claim 21, wherein said cognitive or neurodegenerative disease is Alzheimer's disease.

24. A method of treating Senile Dementia or Alzheimer's disease comprising administering to a patient suffering from said disease a combination of at least one compound according to claim 1 with at least one acetylcholinesterase inhibitor.

25. The method of treating Senile Dementia or Alzheimer's disease according to claim 24, wherein the amount of compound of formula I and amount of inhibitor administered is a therapeutically effective amount.

26. The method of treating Senile Dementia or Alzheimer's disease according to claim 24, wherein the amount of compound of formula I and amount of inhibitor administered are each independently from about 0.001 mg/kg to about 100 mg/kg of body weight.

* * * * *

UNITED STATES PATENT AND TRADEMARK OFFICE
CERTIFICATE OF CORRECTION

PATENT NO. : 6,890,936 B2  
APPLICATION NO. : 10/425376  
DATED : May 10, 2005  
INVENTOR(S) : Craig D. Boyle, William J. Greenlee and Samuel Chackalamannil Page 1 of 1

It is certified that error appears in the above-identified patent and that said Letters Patent is hereby corrected as shown below:

In the Claims:

Claim 22, col. 38, line 47:   Please correct "claim 21" to

-- claim 20 --.

Claim 23, col. 38, line 51:   Please correct "claim 21" to

-- claim 20 --.

Signed and Sealed this

Seventeenth Day of June, 2008

JON W. DUDAS  
*Director of the United States Patent and Trademark Office*